United States Patent
Chapus

(12) 
(10) Patent No.: US 6,432,400 B1
(45) Date of Patent: Aug. 13, 2002

(54) SPECIFIC PANCREATIC LIPASE INHIBITORS AND THEIR APPLICATIONS

(75) Inventor: Catherine Chapus, Marseilles (FR)

(73) Assignee: Laboratoire Laphal (Laboratoire de Pharmacologie Appliquee), Allauch (FR)

( * ) Notice: Subject to any disclaimer, the term of this patent is extended or adjusted under 35 U.S.C. 154(b) by 0 days.

(21) Appl. No.: 09/341,184

(22) PCT Filed: Jan. 6, 1998

(86) PCT No.: PCT/FR98/00009

§ 371 (c)(1),
(2), (4) Date: Sep. 27, 1999

(87) PCT Pub. No.: WO98/30588

PCT Pub. Date: Jul. 16, 1998

(30) Foreign Application Priority Data

Jan. 7, 1997 (FR) ............................................ 97 00071

(51) Int. Cl.[7] .............................................. C07K 14/47
(52) U.S. Cl. ........................... 424/94.6; 435/198; 514/2
(58) Field of Search ............................. 435/198; 514/2; 424/94.6

(56) References Cited

FOREIGN PATENT DOCUMENTS

EP        0 399 379        11/1990

OTHER PUBLICATIONS

Bousset–Risso M. et al.: "Limited proteoloysis of porcine pancreatic lipase. Lability of the Phe 335—Ala 336 bond towards chymotrypsin" FEBS Letters, vol. 182, No. 2, Mar. 1985, Amsterdam NL, pp. 323–326, XP002041837.

Chapus C. et al.: Role of colipase in the interfacial adsorption of pancreatic lipase at hydrophilic interfaces FEBS Letters, vol. 58, No. 1, Oct. 1975, Amsterdam NL, pp. 155–158, XP002041838.

Mahe–Gouhier N. and Leger C.L.: "Immobilized colipase affinities for lipases B, A, C, and their terminal peptide (336–449): the lipase recognition site lysine residues are located in the C–terminal region" Biochimica et Biophysica Acta, vol. 962, 1988, Amsterdam, NL, pp. 91–97, XP002041839.

Melia A.T. et al.: "The effect of orlistat, an inhibitor of dietary fat absorbtion, on the absorbtion of vitamins A and E in healthy volunteers" Journal of Clinical Pharmacology, vol. 36, No. 7, Jul. 1996, pp. 647–653, XP002043023.

Cheng Q. et al.: "C–terminal domain of apolipoprotein C II as both activator and competitive inhibitor of lipoprotein lipase" Biochemistry Journal, vol. 269, No. 2, Jul. 15, 1990, pp. 403–407, XP002043024.

Primary Examiner—Leon B. Lankford, Jr.
(74) Attorney, Agent, or Firm—Morgan, Lewis & Bockius LLP

(57) ABSTRACT

The invention concerns specific pancreatic lipase inhibitors and their applications in the treatment and prevention of cardiovascular diseases, of lyperlipemia and of obesity, as well as diagnostic reagent and as regulating agent in a process of controlled lipolysis of triglycerides. Said inhibitors correspond in particular to a peptide consisting of a C-terminal fragment of pancreatic lipase including the recognition site of a colipase.

6 Claims, 4 Drawing Sheets

SPECIFIC PANCREATIC LIPASE INHIBITORS AND THEIR APPLICATIONS

The present invention relates to specific pancreatic lipase inhibitors and to their applications in the treatment and prevention of cardiovascular diseases, of hyperlipemia and of obesity, and also as diagnostic reagent and as regulating agent in a method of controlled lipolysis of triglycerides.

Dietary fats represent an efficient source of energy for the body. Indeed, the quantity of energy metabolized from lipids is significantly greater than that metabolized from carbohydrates or proteins. However, given that practically all the lipids ingested are assimilated by the body, a dietary excess of lipids can cause substantial health disorders: cardiovascular disorders, hyperlipemias and obesity.

These disorders are frequently encountered in industrialized countries where the populations often have diets which are too high in saturated fats.

In order to combat these various pathological conditions, a dietary care consisting in limiting the ingestion of fatty substances is necessary but not always sufficient. Indeed, while some fatty substances are easy to detect and to remove from the diet (butter, oils and the like), this is considerably less true of others by virtue of their integration into the foods (meats, dairy products and the like).

In the cases where the introduction of a dietary regime proves insufficient, pharmacological treatments are then proposed. Most of the current treatments are intended in particular to combat hyperlipemias by using, inter alia, inhibitors of the synthesis of cholesterol.

However, current research is increasingly geared towards products which induce a more general inhibition of the lipolytic activity.

In such a perspective, one of the orientations which has been particularly studied is that of the inhibition of pancreatic lipase, which is a key enzyme in the digestion of dietary triglycerides; the digestion of the latter, major constituents of lipids (about 95%), which is started in the upper digestive tract by lipases of preduodenal origin (gastric lipase in humans), is essentially carried out in the intestine, under the action of pancreatic lipase. The latter converts the triglycerides to free fatty acids and to 2-monoglycerides, more polar products of hydrolysis, which are capable of crossing the enterocyte brush border membrane, after incorporation into mixed micelles of bile salts and phospholipids.

Pancreatic lipase therefore plays a role in the emergence of diseases linked to the presence of an excess of lipids, such as cardiovascular diseases, hyperlipemias and obesity, by allowing the assimilation of practically all the triglyercides ingested. In addition, it promotes the intestinal absorption of cholesterol, since the solubility of cholesterol is increased in the mixed micelles, which are high in fatty acids.

The action of pancreatic lipase comprises several stages: adsorption of the enzyme, in the intestine, onto the lipid interface, in the presence of bile salts and of a colipase, whose role is to anchor the lipase onto the interface (C. Chapus et al., FEBS Letters, 1975, 58, 1, 155–158), followed by the hydrolysis of the sn-1,3 ester bonds of the triacylglycerols.

Thus, the digestion of triglycerides involves lipase/colipase interactions regulated by a lipid interface.

Porcine lipase, for example, is a glycoprotein containing 449 amino acids, whose glycan chains are linked to asparagine (Asn) at position 166; it contains two domains separated by the $Phe^{336}$-$Ala^{337}$ bond (M. Bousset-Risso et al., FEBS Letters, 1985, 182, 2, 323–326). Each domain carries a recognition site, namely: an interfacial recognition site (N-terminal domain), site of the hydrolysis per se, and a recognition site for its protein partner (C-terminal domain), the colipase. The N-terminal domain (residues 1–335), which carries the active centre of the enzyme, is separated from the C-terminal domain (residues 336–449) by a narrow region which is very resistant to proteolysis. This organization into two domains corresponds to the two specific functions listed above: the N-terminal domain is responsible for catalysis, whereas the C-terminal domain is involved in the recognition of the colipase (A. Abousalham et al., Protein Engineering, 1992, 5, 1, 105–111).

The colipase is a small molecule (10 kDa) which is highly cross-linked because of the presence of 5 disulphide bridges. It carries three recognition sites which are essential for its function, namely: an interfacial recognition site (H. van Tilbeurgh et al., Nature, 1993, 362, 814–820), a lipase recognition site (C. Chaillan et al., FEBS Letters, 1989, 257, 2, 443–446; H. van Tilbeurgh et al., Nature, 1992, 359, 159–162) and a micellar recognition site (J. Hermoso et al., EMBO J., 1997, 16, 18, 5531–5536). These three sites are topologically distinct.

Extensive studies which have been carried out for many years have made it possible to increase understanding of the structure/function relationships in the pancreatic lipase/colipase system (C. Chaillan et al., 1989, cited above).

Additional structural studies relating to both human lipase (Winkler F. K. et al., Nature, 1990, 343, 771–774) and horse lipase (B. Kerfelec et al., Eur. J. Biochem., 1992, 206, 279–287; Y. Bourne et al., J. Mol. Biol., 1994, 238, 709–732) have made it possible to confirm the existence of the abovementioned two domains, in lipases of different origins.

The recognition between the lipase and the colipase involves, in particular, hydrophobic interactions (N. Mahé-Gouhier et al., BBA, 1988, 962, 91–97) and electrostatic interactions.

Covalent coupling experiments between the pancreatic lipase and colipase (C. Chaillan et al., 1989, cited above), as well as the resolution of the three-dimensional structure at 3.1 Å of the lipase/colipase complex (H. van Tilbeurgh et al., 1992, cited above), have led to the identification of the recognition regions on the two molecules, in solution.

To inhibit pancreatic lipase and obtain a therapeutic activity on hyperlipemias and obesity, various approaches have been proposed:

the use of covalent inhibitors, which bind to the active centre of the enzyme; there may be mentioned, for example, tetrahydrolipstatin (THL), [U.S. Pat. No. 4,598,089; P. Hadvary et al., J. Biol. Chemistry, 1991, 266, 4, 2021–2027; D. Hermier et al., FEBS Letters, 1991, 286, 1, 186–188]; a complete inhibition of the lipolytic activity is obtained for doses of 1 mol of THL/mol of enzyme (P. Hadvary et al., 1991, cited above) or doses of 10 to 400 mg, twice per day (J. Hauptman et al., Am. J. Clin. Nutr., 1992, 55, 309S-313S); such a method has a number of disadvantages, of which the main one is the lack of specificity; tetrahydrolipstatin is indeed not specific for pancreatic lipase and inhibits other lipases such as carboxylester lipase, gastric lipase and lipase stimulated by the bile salts in human milk; and the modification of the nature of the interface by addition of amphiphilic proteins (Gargouri Y. et al., J. Biol. Chem., 1985, 260, 2268–2273); of detergents (Gargouri Y. et al., J. Lip. Res., 1983, 24, 1336–1342) or of fibres (Borel P. et al., Am. J. Clin. Nutr., 1989, 49, 1192–1202); such a method has a very relative efficiency.

These two approaches comprise, in addition, a significant risk of undesirable effects (nausea and the like).

Consequently, the applicant set itself the objective of providing a new pancreatic lipase inhibitor which is better suited to the needs of practical application than the prior art lipase inhibitors, in particular in that it exhibits a real specificity of action towards pancreatic lipase.

The subject of the present invention is a peptide consisting of a C-terminal fragment of a pancreatic lipase, including the recognition site for a colipase (called hereinafter C-terminal peptide), for its use as medicament, in particular for the treatment of hyperlipemias, of cardiovascular diseases and of obesity.

According to an advantageous embodiment of the invention, the said peptide is a C-terminal fragment of a pancreatic lipase selected from purified or recombinant human, porcine or equine pancreatic lipases.

Unexpectedly, the C-terminal peptide of these various pancreatic lipases effectively makes it possible for them to serve as a lure and to competition between this peptide and the native lipase for the colipase and thus to significantly reduce the lipolytic action of the said lipase.

The administration of such a peptide slows down the action of the pancreatic lipase and surprisingly inhibits, at least in part, the hydrolysis of dietary triglycerides, which will therefore not be absorbed (inhibitory effect of the C-terminal peptide on the lipolysis).

Indeed, the affinity of this C-terminal peptide is, in vitro:
in solution, of the order of $10^6$ M, towards the colipase, whereas
at the lipid interface, the affinity of the C-terminal peptide is of the order of $2 \times 10^8$ M.

To obtain the desired action, that is to say an affinity at the interface of the order of $2 \times 10^8$ M, the said C-terminal peptide is preferably administered at doses of 0.5 to 10 mg/day distributed over 1 to 3 takings, corresponding to doses of 0.2 to 10 mg per taking.

The subject of the present invention is also a pharmaceutical composition comprising the C-terminal peptide of a pancreatic lipase, including the recognition site for a colipase, as defined above and at least one pharmaceutically acceptable vehicle.

The said pharmaceutical composition is advantageously provided in a unit form capable of being administered by the oral route, selected from the group consisting of soft or hard gelatin capsules, tablets, solutions, suspensions and emulsions.

Such a pharmaceutical composition is preferably intended for oral administration, in a gastroresistant form.

The subject of the present invention is also other applications of the said C-terminal peptide of pancreatic lipase, for example as diagnostic reagent, in particular in the carrying out of an immunoenzymatic test for the assay of lipase by a competitive-type method and in the carrying out of methods of controlled lipolysis of triglyceride substrates.

In addition to the preceding features, the invention also comprises other features which will emerge from the description which follows, which refers to exemplary embodiments of the present invention, as well as to the accompanying drawings, in which.

Figure 1:
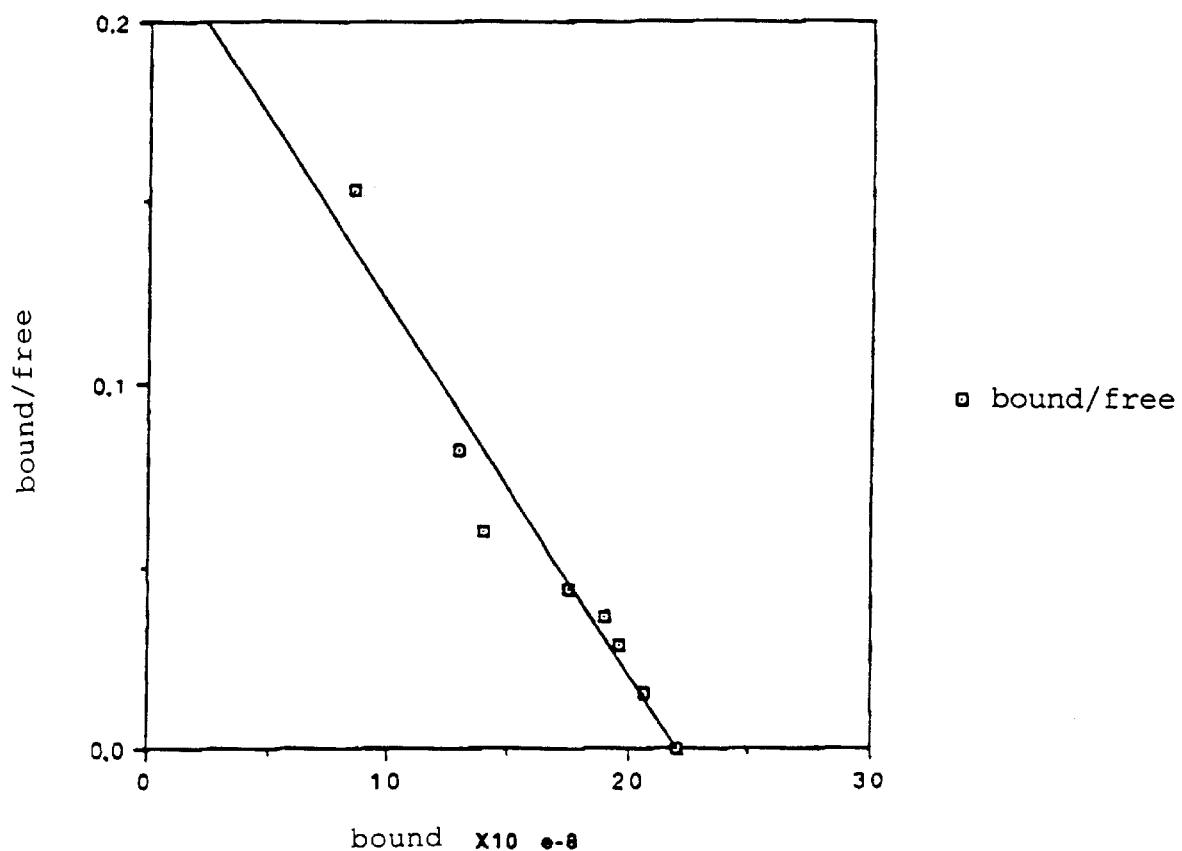
FIGS. 1 and 2 represent the Scatchard plots obtained from differential spectra [(colipase-C-terminal peptide)-C-terminal peptide] in aqueous solution for FIG. 1 and in the presence of a tributyrin/water interface for FIG. 2.

It should be clearly understood, however, that these examples are given solely by way of illustration of the subject of the invention and do not constitute in any manner a limitation thereto.

EXAMPLE 1

Isolation of the Pig C-terminal Peptide

Purification of the pancreatic lipase and of the colipase

The porcine pancreatic lipase is purified as described in Rovery M. et al. (Biochim. Biophys. Acta, 1978, 525, 373–379), from an acetone pancreatic powder.

The purification of the pig colipase is carried out according to C. Chapus et al. (Eur. J. Biochem., 1982, 115, 99–105).

The protein concentrations are determined at 280 nm, using a molecular absorption coefficient of $6.65 \times 10^4$ M$^{-1}$ cm$^{-1}$ for the lipase and of $0.4 \times 10^4$ M$^{-1}$ cm$^{-1}$ for the colipase.

Production, purification and analysis of the C-terminal peptide of the pig pancreatic lipase 100 mg of porcine lipase are dissolved in 20 ml of 60 mM ammonium bicarbonate buffer, pH 8.5, containing 1 mM benzamidine.

1 mg of TLCK(tosyl lysine-chloromethyl ketone)-treated chymotrypsin is added and the mixture is incubated at 37° C. for 18 hours. Aliquots are collected at various times, analysed by SDS-PAGE and tested for their lipase activity.

The chymotrypsin attack is stopped by addition of 0.2 mM PMSF (phenylmethylsulphonyl fluoride).

The digestion mixture is subjected to molecular sieving on an Ultrogel AcA 54 column (2.5×200 mm), equilibrated with a 10 mM Tris-HCl buffer, pH 7.5, containing 0.2 M NaCl and 1 mM benzamidine; the elution is carried out with the same buffer.

The amino acid analysis is carried out with an automated analyser (Beckman 6300), after 24 hours of hydrolysis of the samples, in sealed tubes containing 6 M triple-distilled HCl. The N-terminal sequence of the peptide is obtained by degradation, according to the Edman method, using a sequencer (Applied Biosystems 470A). The phenylthiohydantoins obtained are analysed by HPLC (C18 column, Brownlee, 5 µm, 2.1×220 mm). They are eluted using a methanol gradient (10–46%) in a 5 mM sodium acetate buffer, pH 4.84.

The fragments obtained are subjected to a gel electrophoresis (SDS-PAGE), according to the Laemmli U. K. technique (Nature, 1970, 227, 680–685). The proteins and the peptide fragments are stained with Coomassie brilliant blue and gel slices are destained with the aid of an ethanol:acetic acid:water mixture (5:7.5:87.5 vol/vol).

The peptides generated by the proteolytic attack are loaded, in duplicate, onto fragments of 18% polyacrylamide gel and separated by electrophoresis in the presence of SDS.

After transferring onto PVDF (polyvinylidene difluoride), one lane is stained so as to locate the C-terminal peptide and the other is cut out so as to carry out the sequencing of this sequence.

The analysis of the C-terminal peptide, isolated and purified, by SDS-PAGE, as well as the amino acid analysis, shows that this peptide has the molecular weight and the expected amino acid composition (see N. Mahé-Gouhier et al., 1988, cited above and M. Bousset-Risso et al., 1985, cited above). The sequencing of the N-terminal portion of the chain exhibits the following sequence: Ala-Arg-Trp-Arg-Tyr-Lys-Val-Ser, showing clearly that chymotrypsin cleaves the sequence at the level of the Phe$^{336}$-Ala$^{337}$ bond, which is the junction of the C- and N-terminal domains of pancreatic lipase.

EXAMPLE 2

Demonstration of the Porcine Lipase C-terminal Peptide Interaction with the Colipase, in Aqueous Solution The C-terminal domain/colipase interaction in aqueous. medium (in the absence of lipid interface) was measured by spectrofluorometry.

The fluorescence emission spectra of the C-terminal peptide are recorded on a Kontron spectrofluorometer (SFM235), equipped with a thermostated cell and a magnetic stirring system. This spectrofluorometer is in addition connected to a computer (Apple IIe).

All the experiments were carried out at 25° C. and at pH 7.5. The excitation wavelength of 290 nm was chosen because the pig pancreatic colipase contains no tryptophan residues and the changes in fluorescence emission can thus be attributed to the tryptophan residues of the C-terminal peptide, when it interacts with the colipase.

The fluorescence emission spectrum of the C-terminal peptide at a final concentration of $0.26 \times 10^{-6}$ M in 10 mM Tris-HCl buffer, pH 7.5, containing 0.1 M NaCl, is measured between 300 and 400 nm. The colipase stock solution is prepared in the same buffer; the colipase concentration varies from $2.8 \times 10^{-8}$ to $1.4 \times 10^{-6}$ M.

The evaluation of the dissociation constant is determined using the following Scatchard formula:

$$\frac{L_b}{L_f} = \frac{nP_o}{K_d} - \frac{L_b}{K_d}$$

in which $L_b$ and $L_f$ correspond to the concentrations of bound colipase and of free colipase at equilibrium, $P_o$ the total concentration of C-terminal peptide and $K_d$ the dissociation constant.

Results

The differential spectra [(colipase-C-terminal peptide)-C-terminal peptide] show a reduction in the fluorescence emission. The Scatchard plots obtained from these spectra make it possible to evaluate the colipase/C-terminal peptide dissociation constant at $10^{-6}$ M in solution, under the conditions specified above (FIG. 1).

In this FIG. 1, the x-axes represent the quantity of bound C-terminal peptide [complex colipase/C-terminal (TC)] and the y-axes represent the bound C-terminal peptide/free C-terminal peptide ratio [complex colipase/C-terminal (TC)/ free C-terminal (C) (TC/T)].

EXAMPLE 3

Demonstration of the Porcine Lipase C-terminal Domain Interaction with the Colipase and Inhibitory Action in vitro on the Lipase, at the Interface (Substrate: Tributyrin)

conditions for measuring the inhibition of the lipase and colipase activities by the C-terminal peptide of the lipase, in the presence of an interface The lipase activity is measured by titrimetry at 25° C. in a medium consisting of 1 mM Tris-HCl buffer at pH 7.5, containing 0.1 M NaCl and 5 mM $CaCl_2$, in the presence of sodium taurodeoxycholate (NaTDC) at a final concentration of 1 mM.

The colipase activity is measured under the same conditions, but in the presence of 4 mM NaTDC.

The final volume is 15 ml; the substrate used is emulsified tributyrin, at a final concentration of 0.11 M.

The activities are measured in the absence and in the presence of increasing quantities of a stock solution of C-terminal peptide ($10^{-6}$ M)

inhibition of the lipase activity by the C-terminal peptide of the lipase

The lipase/colipase molar ratio is equal to 1 and the final concentration of lipase and of colipase is $0.19 \times 10^{-9}$ M.

The concentration of C-terminal peptide varies from $0.2 \times 10^{-9}$ to $30 \times 10^{-9}$ M.

The maximum rate of inhibition of the lipase activity recorded under these conditions is about 50%.

inhibition of the colipase activity by the C-terminal peptide of the lipase

Figure 2:
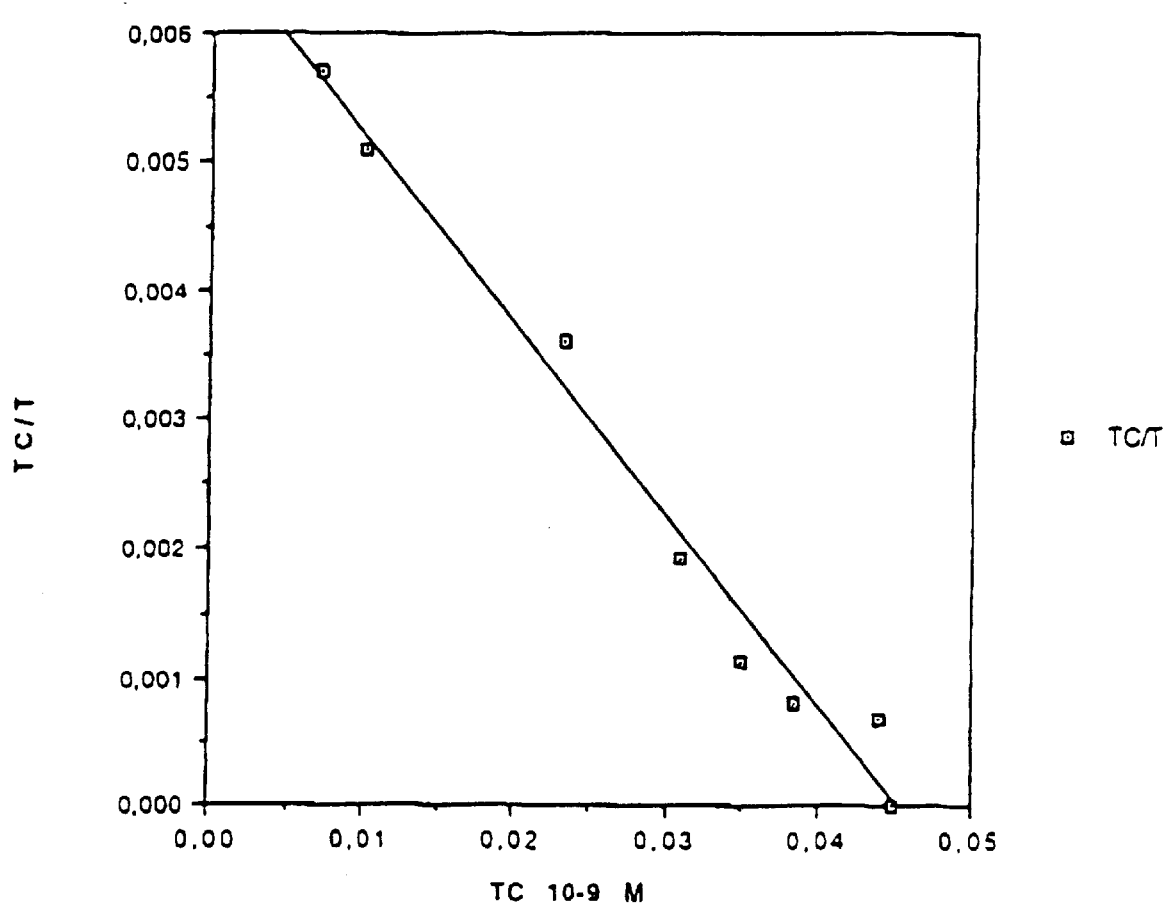

The lipase/colipase molar ratio is equal to 0.75 (lipase $0.19 \times 10^{-9}$ M; colipase $0.25 \times 10^{-9}$ M). The concentration of C-terminal peptide varies as above. The maximum rate of inhibition of the colipase activity recorded is also 50%. The dissociation constant estimated from the Scatchard plot is $2 \times 10^{-8}$ M (FIG. 2).

These results show that, in solution, the affinity of the colipase for the C-terminal peptide is of the same order of magnitude as the affinity of the colipase for the lipase and that this affinity is increased by a factor of 50 to 100 in the presence of a tributyrin/water interface.

EXAMPLE 4

Demonstration of the Interaction of the C-terminal Domain of the Lipase with the Colipase in the Presence of a Lipid Interface: Inhibition of the Lipase Activity by the C-terminal Domain in vitro (Physiological Substrate: Emulsified Triolein)

The kinetic studies of inhibition of the lipase by the C-terminal domain were carried out in the presence of a more physiological lipid interface than in Example 3, the substrate used being emulsified triolein.

The activity of the lipase is measured by titrimetry with the aid of a pH stat, at 25° C., on a triolein emulsion under conditions where the activity of the enzyme is strictly dependent on the presence of the colipase.

The reaction medium (15 ml) contains:

8 mM triolein 4 mM sodium taurodeoxycholate 1 mM Tris/HCl, pH 7.5, 5 mM $CaCl_2$, 0.1 M NaCl.

The competition experiments are carried out in the presence of native lipase and colipase and of the C-terminal domain obtained by proteolysis.

Inhibition of the lipase activity by the C-terminal domain:

The final concentrations of lipase and colipase are $1.7 \times 10^{-9}$ M and $1.4 \times 10^{-9}$ M respectively.

The lipase/colipase molar ratio is equal to 1.2. For a concentration of C-terminal domain equal to $2 \times 10^{-7}$ M, the maximum rate of inhibition observed is about 50%.

EXAMPLE 5

Demonstration of the Interaction of the C-terminal Domain of the Porcine Lipase with the Colipase and Inhibitory Action in vitro on the Lipase, at the Interface, Under More Physiological Conditions (Substrate: Triolein, Phospholipids and Total Bile Salts)

Figure 3:
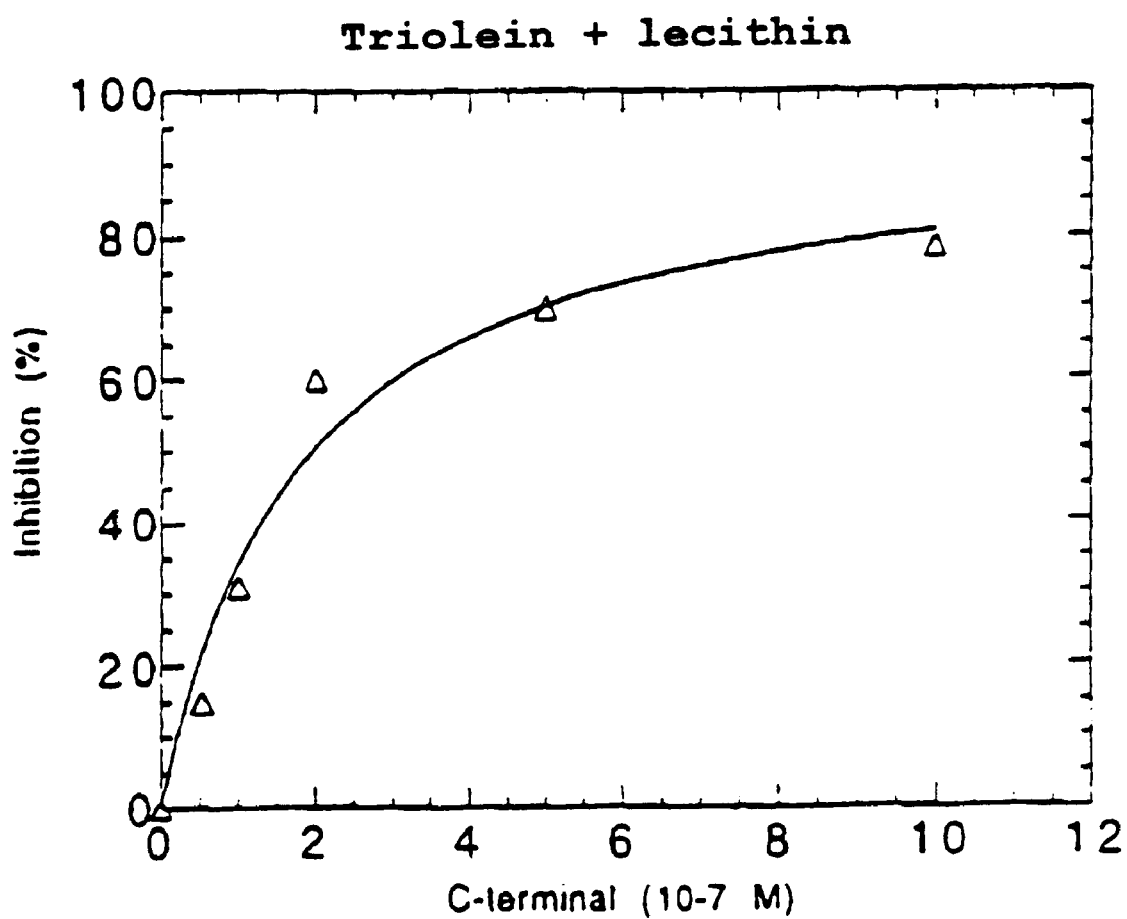
FIGS. 3 and 4 represent the inhibition of the lipase activity by the C-terminal peptide of the lipase (substrate: triolein, phospholipids, total bile salts) in the absence (FIG. 3) or in the presence (FIG. 4) of oleic acid.
Figure 4:
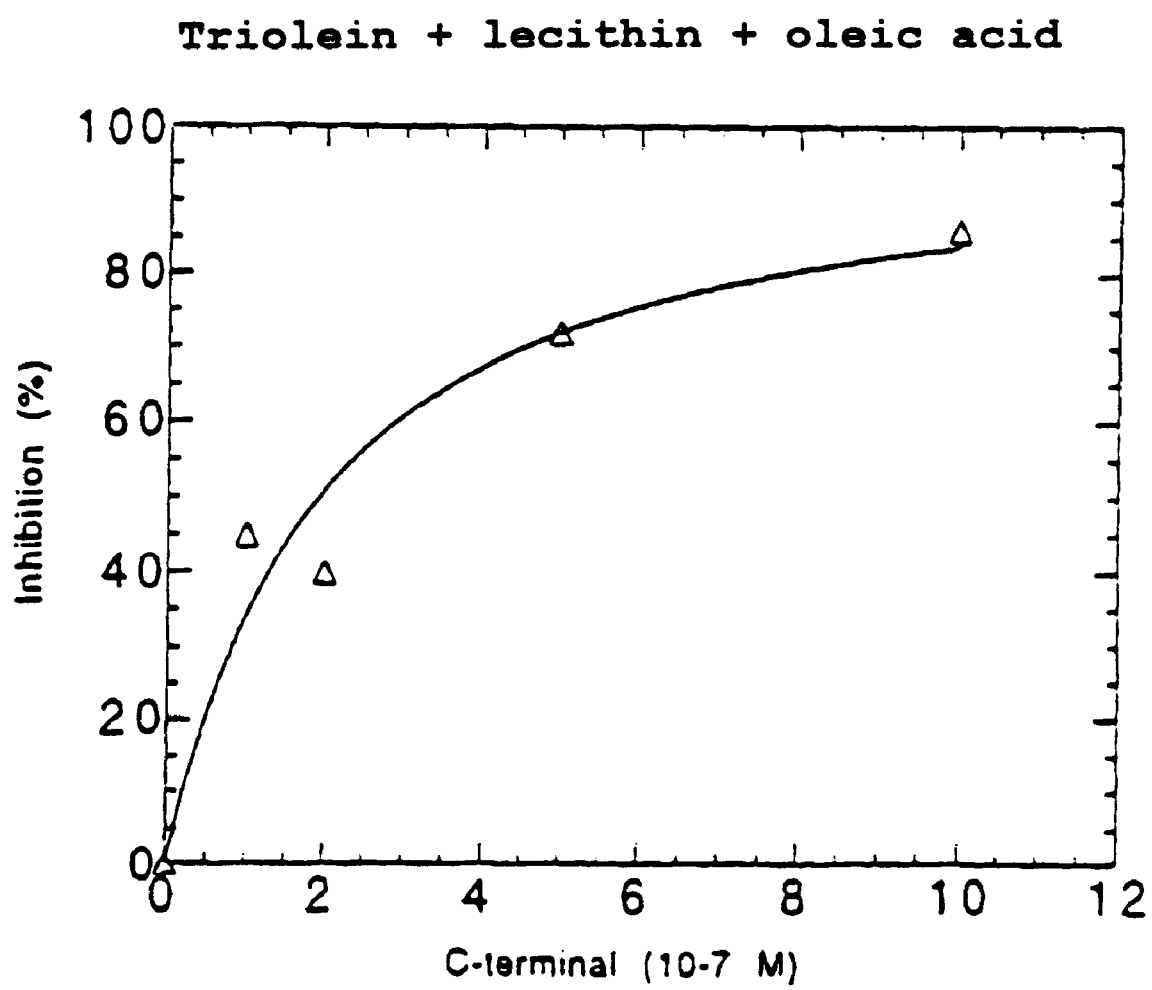

The inhibition of the lipase activity by the C-terminal peptide of the lipase is measured as described in Example 3, but the substrates used consist of emulsions of long-chain triglycerides (10 mM triolein) in the presence of phospholipids (triolein/lecithin ratio=20) and of a mixture of total bile salts (6 mM) in the absence (FIG. 3) or in the presence (FIG. 4) of oleic acid (5 mM). The oleic acid is a product of lipolysis. On the arrival of the food bolus in the duodenum, a portion of the dietary triglycerides was hydrolysed and long-chain fatty acids (such as oleic acid) are present in the duodenum. These free fatty acids will combine with the bile secretion and also find themselves in part at the lipid interface. They therefore play a role in lipolysis.

Results:

In all cases, 50% inhibition of the lipolysis is obtained in the presence of $2 \times 10^{-7}$ M C-terminal peptide, which represents a 5-fold increase in the affinity of the C-terminal domain for the colipase in the presence of the lipid interface, in comparison with the values obtained in the absence of the lipid interface (FIG. 1).

As is evident from the above, the invention is not at all limited to its embodiments, implementations and applications which have just been described more explicitly; it embraces, on the contrary, all the variants which may occur to the specialist in this field, without departing from the framework or from the scope of the present invention.

I claim:

1. A method of treating disorders linked to an excess of lipids, comprising: administering to a person in need thereof, an effective amount of a peptide comprising a C-terminal fragment of a pancreatic lipase that contains a recognition site for a colipase, wherein said colipase carries three topologically distinct recognition sites: an interfacial recognition site, a lipase recognition site and a micellar recognition site.

2. The method according to claim 1, wherein said lipase is selected from the group consisting of: purified human pancreatic lipases, purified porcine pancreatic lipases, purified equine pancreatic lipases, recombinant human pancreatic lipases, recombinant porcine pancreatic lipases, and recombinant equine pancreatic lipases.

3. The method according to claim 1, wherein the disorder linked to an excess of lipids is hyperlipemia.

4. The method according to claim 1, wherein the disorder linked to an excess of lipids is obesity.

5. The method according to claim 1, wherein the disorder linked to an excess of lipids is a cardiovascular disorder.

6. A method of inhibiting the enzymatic lipolysis of triglyceride substrates, comprising the steps of:
   a. forming an admixture of a pancreatic lipase, its colipase, carrying three topologically distinct recognition sites: an interfacial recognition site, a lipase recognition site and a micellar recognition site, and a triglyceride substrate in an amount and under conditions effective for lipolysis of the substrate; and
   b. adding a peptide comprising a C-terminal fragment of a pancreatic lipase that contains a recognition site for a colipase to the lipase/colipase/substrate admixture in an amount effective to inhibit the lipolysis of the substrate.

* * * * *